United States Patent
Venturini et al.

(10) Patent No.: US 6,749,611 B2
(45) Date of Patent: Jun. 15, 2004

(54) BONE SCREW, PARTICULARLY FOR USE WITH EXTERNAL FIXATORS IN FRACTURE STABILIZATION

(75) Inventors: Daniele Venturini, Povegliano Veronese (IT); Luigi Rossi, Peschiera Del Garda (IT)

(73) Assignee: Orthofix S.r.l. (IT)

( * ) Notice: Subject to any disclaimer, the term of this patent is extended or adjusted under 35 U.S.C. 154(b) by 0 days.

(21) Appl. No.: 10/275,527

(22) PCT Filed: Feb. 26, 2001

(86) PCT No.: PCT/EP01/02184

§ 371 (c)(1), (2), (4) Date: Nov. 5, 2002

(87) PCT Pub. No.: WO01/85042

PCT Pub. Date: Nov. 15, 2001

(65) Prior Publication Data

US 2003/0093076 A1 May 15, 2003

(30) Foreign Application Priority Data

May 5, 2000 (EP) .............................................. 00830331

(51) Int. Cl.⁷ .......................... A61B 17/58; F16B 23/00
(52) U.S. Cl. .......................... 606/54; 606/73; 411/401; 411/424
(58) Field of Search .............................. 606/53, 54, 59, 606/60, 72, 73, 104; 433/221, 225; 411/378, 385, 398, 401, 424, 411, 417

(56) References Cited

U.S. PATENT DOCUMENTS

| | | | | |
|---|---|---|---|---|
| 3,920,343 A | | 11/1975 | Blue et al. | |
| 4,342,309 A | * | 8/1982 | Eftekhar | 602/37 |
| 4,628,921 A | * | 12/1986 | Rousso | 606/54 |
| 4,692,116 A | | 9/1987 | Filhol | |
| 4,796,612 A | * | 1/1989 | Reese | 606/72 |
| 5,087,259 A | * | 2/1992 | Krenkel | 606/60 |
| 5,443,464 A | * | 8/1995 | Russell et al. | 606/54 |

FOREIGN PATENT DOCUMENTS

| | | |
|---|---|---|
| EP | 1042988 A1 | 10/2000 |
| FR | 2692471 A1 | 12/1993 |
| FR | 2765094 A1 | 12/1998 |

* cited by examiner

Primary Examiner—Eduardo C. Robert
Assistant Examiner—David Comstock
(74) Attorney, Agent, or Firm—Akerman Senterfitt

(57) ABSTRACT

The invention relates to a bone screw, particularly for use with external splints in fracture stabilization, comprising an elongate cylindrical body (2) of predetermined length and diameter tapering into a threaded end portion (5) which terminates with a tip (6), and an opposite screw-handling end (3). The screw-handling end (3) has substantially the same diameter as that of the elongate cylindrical body (2) and comprises a flat (7) extending parallel to the axis of the cylindrical body over the main part of the cylinder body portion unoccupied by the thread. In a further embodiment, the screw-handling end (3) is formed with a plurality of flats (8) extending parallel to the axis of the cylinder body (2) at predetermined spacings. These flats extend over the main part of the cylindrical body portion unoccupied by the threadway and alternate with lands (9).

7 Claims, 2 Drawing Sheets

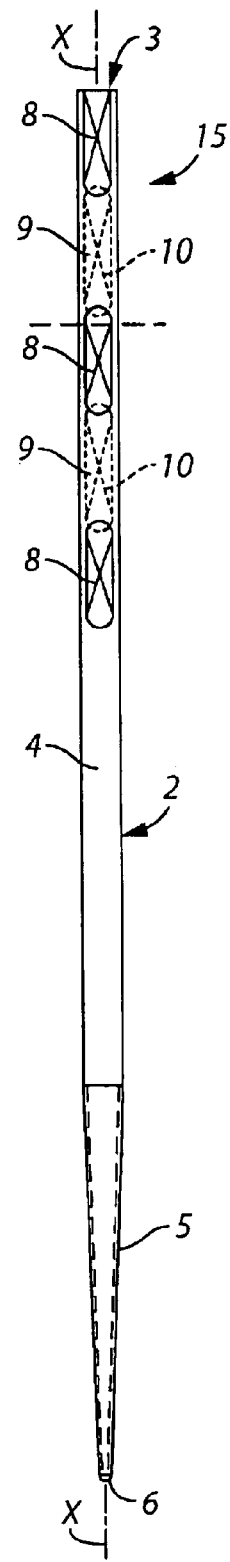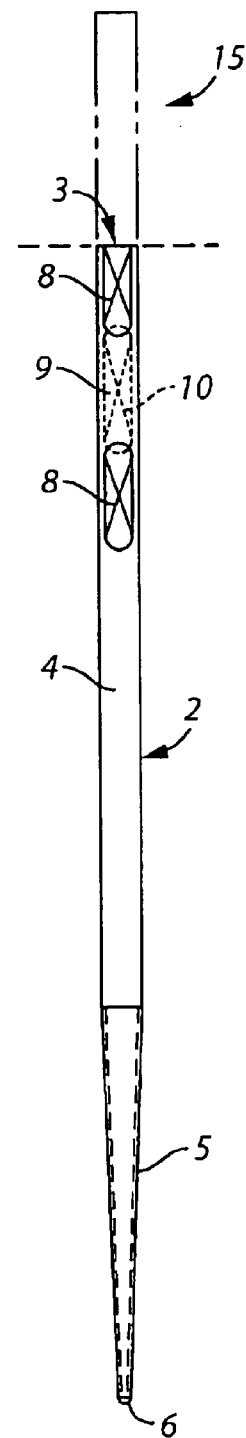
FIG. 2  FIG. 3

BONE SCREW, PARTICULARLY FOR USE WITH EXTERNAL FIXATORS IN FRACTURE STABILIZATION

DESCRIPTION

1. Field of the Invention

This invention broadly relates to a bone screw useful for fastening external splints, as applied to a fractured limb by orthopedic surgery in order to stabilize the bone fracture.

In particular, the invention relates to a bone screw having an elongate cylinder body of predetermined length, a threaded end portion terminating with a tip, and an opposite screw-handling end.

2. Prior Art

As it is well known in this specific technical field, one of the most effective methods for stabilizing bone fractures is based on the use of external splints, whereby fractures at particularly delicate locations, e.g. close to the joints, or fractures with attendant serious injury of the cutaneous tissue, can be set in all those cases in which the traditional plaster could be unsuitable or even impracticable.

Such splints are fastened at their opposite ends to respective undamaged portions of the broken bone, specifically to opposite sides of the fracture. The splint ends are fastened by means of bone screws which are firmly implanted in the bone itself.

In the instance of a tibial fracture, for example, the opposite ends of a respective tibial external splint are fastened on either sides of the fracture using appropriate bone screws. In other instances, when the fracture affects a joint, such as an ankle, the bone screws of a respective ankle external splint are implanted into the tibia and the talus.

These bone screws are to provide reliable anchor points for the external splint device. To this aim, they generally comprise:

- a screw shank, having a substantially elongate cylindrical shape;
- a threaded screw portion, generally tapering toward a tip;
- an opposite screw-handling end, that is a screw head structure and adapted for engagement by a driving tool, such as a wrench or a power driver.

Advantageously, the screw head consists of a short flat lying portion, which is parallel to the screw axis and formed by a milling process at the screw end opposite to the tip.

In view of the bulky size of the above external splint apparatus and of its sticking out in the installed position from one side of the fractured limb, it will be appreciated that a splint device may constitute a bulky interfering attachment for both the operating personnel and the patient. Accordingly, in this field it exists the need of reducing or at least of limiting such encumbrance.

A way of filling this demand is, for example, that of using bone screws of different length and such that the ultimate implanted screws will jut a shorter length out of the splint device.

For the purpose, the prior art provides each splint with a plentiful range of bone screws, all alike in shape and construction but having different lengths. Thus, the orthopedic surgeon will always have the screw with the most appropriate length available for each case, and in the implanted state, the screw will not jut out of the splint device, although its handling end can still be easily reached.

This is a widely accepted and fairly satisfactory solution, but it can not fill the demands of every surgical situation. Besides, it still exhibits technical shortcomings such as—perhaps most importantly—the difficulty represented by the need to select the bone screw with the most suitable length "on the spot", since once the screw implanting operation is in progress using the selected screw, it is inconvenient or impossible to interrupt such operation to substitute said screw with a more suitable one. Because of the difficulty experienced in selecting the screw with the most suitable length "on the spot", it is not infrequent for one or more bone screws to jut out undesirably of the external splint after installation, resulting in the aforementioned drawbacks.

Another shortcoming is the large number of screws that must be made available in order to cover the largest possible number of operative situations, which can occur. On the one side, this makes the selection less obvious, and on the other, weighs heavily on the overall cost for equipment.

FR 2 751 523 discloses a self tapping screw for fixing osteosynthesis plate. The screw comprises a self-tapping threaded shank with a head connected by an intermediate brittle area to a gripping end to be inserted into the barrel of a screw driving tool.

U.S. Pat. No. 5,487,744 discloses a spinal fixation device for immobilizing a portion of a spine which includes at least one spine rod and a plurality of bone screws that are threaded into an appropriate number of vertebrae and each of which includes a threaded end protruding from the vertebra. Clamps are used to fasten a spine rod to the bone screws.

EP 0729731 discloses a fixation system of column constituted by a fitting of vertebral column, a pedicular stem which can be used in the case of a traction as well as in the case of a fracture, a bolt screw provided with a cylindrical recess, a nut and a cylinder shaped bar with flat exterior surface.

U.S. Pat. No. 4,778,388 discloses a root canal post for use in constructing a therapeutic foundation on the root tooth for treatment of a broken tooth, the post comprising a head, a shank and a bore axially produced through the head and shank. The bore includes a filler releasably filled therein so that after the post is anchored in the tooth, a subsequent treatment for a possible secondary cavities is applied through the bore which is made empty by removing the filler.

However, the heads of the screw according to FR 2 751 523 and the post according to U.S. Pat. No. 4,778,388 have a diameter higher than that of their respective shanks, the bolt screw according to EP 0 729 731 is to be allocated into a cylindrical hollow space of the fixation system and the screw according to U.S. Pat. No. 5,487,744 is provided with two opposite threaded ends for anchoring the screw in a vertebra and for fastening the screw to the clamp respectively.

Due to the above characteristics, all the screws according to FR 2 751 523, U.S. Pat. No. 4,778,388, EP 0 729 731 and U.S. Pat. No. 5,487,744 have a fixed length and therefore display the same inconveniences as those of the above-cited prior art screws.

U.S. Pat. No. 6,004,327 discloses a ratcheting compression device which can be customized in length and comprises two pieces, of which one is a pin comprising an elongate cylindrical body of predetermined length having located at or near its distal end a threaded portion and having preferably a substantially smooth portion at or near its proximal end.

However, although the threaded portion of the pin terminates with a tip, a substantial part of the above threaded portion has an outside diameter which is higher than the diameter of the cylindrical body.

Furthermore, the pin is provided near its mid portion with ratcheting means, preferably asymmetric teeth, which cooperate with anti-rotation means provided on the other piece of the device according to U.S. Pat. No. 6,004,327 in order to compress two segments of bone together.

The underlying technical problem of this invention is to contrive a bone screw with structural and functional features able to overcome the aforementioned disadvantages. The invention devises a "universal" bone screw, which allows a substantially univocal selection of such screw in all types of external splint installations, and drastically cuts down the expenses due to the necessity of requiring a comprehensive set of screws which are similar in structure, but have different lengths.

SUMMARY OF THE INVENTION

The principle of this invention is to have a handling end of the screw of substantially the same diameter as that of the screw body and formed with flats alternating with lands which extend over the main part of the screw body.

Based on this principle, the technical problem is solved by a bone screw as previously indicated and characterized in the following claims.

The features and advantages of a bone screw according to the invention will be apparent in the following description of an embodiment thereof, to be read with reference to the accompanying non-limitative drawings.

BRIEF DESCRIPTION OF THE DRAWINGS

In the drawings:

FIGS. 2 and 3 are plan views of the screw shown in FIG. 1, respectively full length and as trimmed short.

DETAILED DESCRIPTION

Figure 1:
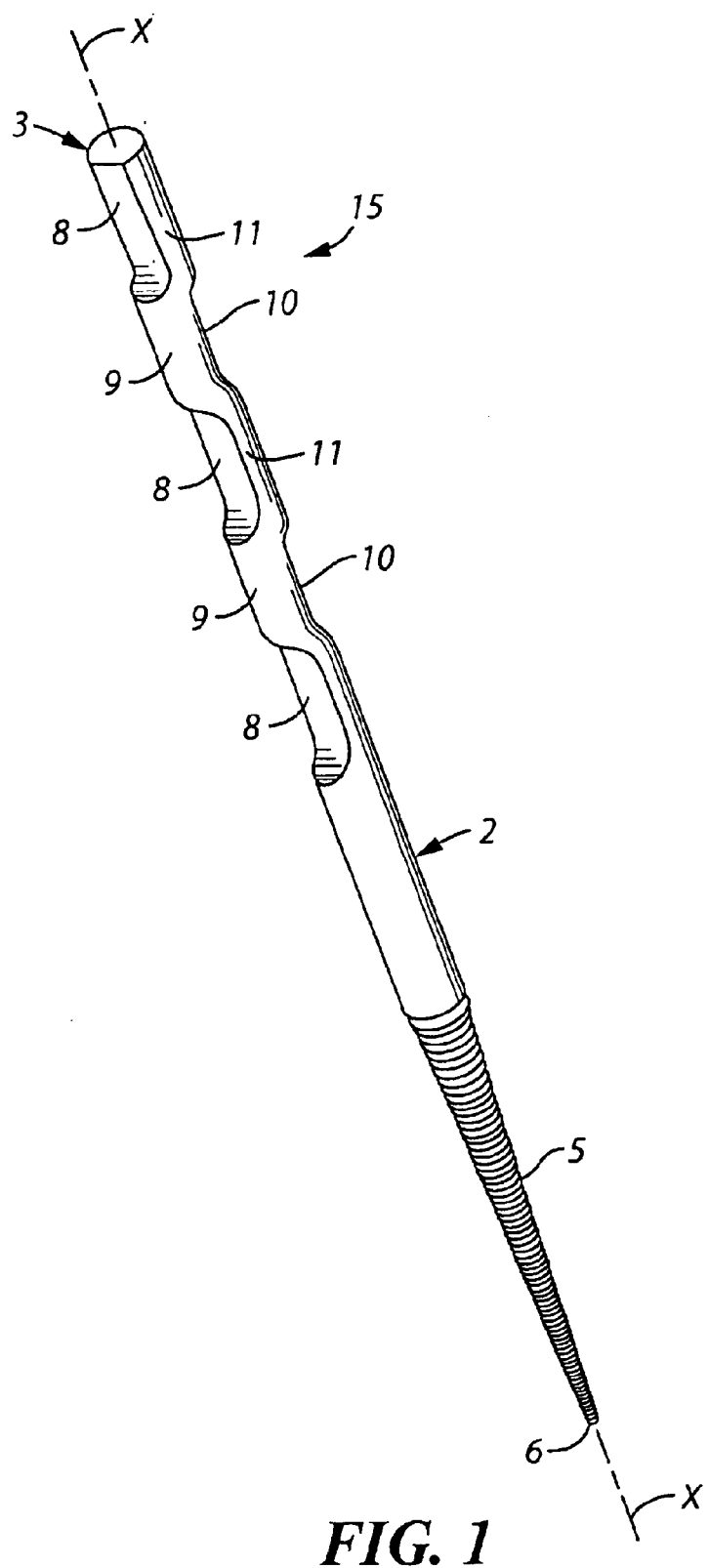
FIG. 1 shows a perspective view of an embodiment of the inventive screw.

Referring to the above drawings, a bone screw according to the invention for fastening external splint apparatuses—as applied in orthopedic surgery to fractured limbs with the purpose to stabilize bone fractures—is generally shown at 1. Such splint apparatuses are not shown in the drawings since they are conventional.

The screw 1 has an elongate cylindrical body 2 of predetermined length. The body 2 has a longitudinal axis X—X and a circular section of predetermined diameter.

The body 2 tapers into an end portion 5 of the screw 1 which is threaded and terminates with a tip 6.

An oppositely located screw-handling end, generally shown at 3, corresponds to the other free end of the cylindrical body 2. This handling end has substantially the same diameter as that of the elongate cylindrical body 2 and is essentially the head of the screw 1.

The elongate cylindrical body 2 of the screw 1 has a smooth main portion 4, referred to as the shank of the screw 1 hereinafter.

Advantageously in this invention, the screw-handling end 3 includes a plurality of rectangular flats 8 aligned with each other and at a predetermined distance apart one from the other.

The flat 7 is rectangular in shape, and in the example of FIG. 1 provided on only one side of the screw shank, such as by a milling operation.

The presence of the provided flat 7, allows to cut the shank of the screw at any location along the flat, as schematically shown in FIG. 4, while maintaining a screw-handling end 3 always available. To facilitate the shank length trimming operation, a plurality of transversal nicks 12 are formed in the cylindrical body 2 to mark the spots for cutting. Such nicks 12 are located at a predetermined distance apart, e.g. provided at a spacing of 20 mm one from the other.

FIG. 2 shows a bone screw according to a second embodiment of the present invention. In the figures, the details of the bone screws structurally and functionally equivalents are indicated by the same reference numbers.

With reference now to FIG. 2, a bone screw 15 formed according to the present invention includes a plurality of rectangular flats 8 aligned with each other and at a predetermined distance apart one from the other.

These flats 8 alternate with lands 9, which practically establish the distance separating the flats.

A flat 8 is joined to a separation land 9 by a radiused step.

The steps provided between flats 8 and lands 9 define abutment shoulders for a tool, such as a T-wrench, employed to operate the bone screw 1 from its handling end. This wrench is omitted from the drawings because conventional.

The flats 8 are preferably the same length throughout. However, it would be possible for the flats 8 to have different lengths.

The flats 7, 8 and 10 are rectangular in shape, and in the example of FIG. 1 are provided respectively on one side of the screw shank, such as by a milling operation.

Advantageously, another plurality of flats 10 are formed in the cylindrical body 2 of the screw 1, correspondingly with and diametrically opposite from said plurality of flats 8.

The flats 10 also alternate with separation lands 11.

More particularly, a separation land 9 of the diametrically opposite plurality of flats 8 corresponds with a flat 10. Conversely, a separation land 11 of the diametrically opposite plurality of flats 10 corresponds with a flat 8.

The flats 10 and the respective separation lands 11 are also joined by a radiused step.

Merely as an example, the screw 1 may be an overall length of 240 mm inclusive of a threaded portion 5, which is 80 mm long.

With a screw 240 mm long, the diameter of the shank 2 is preferably 6 mm long, like the outside diameter of the threaded portion 5 at the shank 2. The outside diameter of the threaded portion then tapers to 5.6 mm at the tip end 6.

The presence of the provided flats 7, 8 and 10 allows the shank of the screw to be cut at any location along the flats, as schematically shown in FIG. 3, while maintaining a screw-handling end 3 always available.

The clearance described by the protruding shank can thus be significantly reduced, while it is still possible to turn the screw 1 for removal by engaging a flat 8 with the aforementioned T-wrench.

The section of the shank 2 to be cut through at the flats is smaller than the circular section, with plural flats 8 being provided.

In fact, the radial thickness of the cylindrical screw body 2 is approximately 5 mm when measured at a flat.

It should be noted, however, that this thickness reduction doesn't significantly lower the breaking point of the screw under a high torque.

Thus, the invention solves the technical problem by providing a universal bone screw effective to reduce the need to maintain a set of different length bone screws.

A major advantage is a minimized clearance outline for the splint device.

Another advantage becomes evident at the splint installing stage, when the orthopedic surgeon is no longer to make decisions about the screw size since he can use a single screw type to trim depending on the necessity.

A further advantage is that cutting the shank is facilitated by the reference marks represented by the radiused steps.

Finally, the screw of this invention can be manufactured with large-volume methods.

What is claimed is:

1. A bone screw for use with external splints in fracture stabilization, comprising:
    an elongate cylindrical body of predetermined length and diameter having a smooth shank portion and a tapered threaded end portion which terminates with a tip; and
    an opposite screw-handling end,
    wherein said smooth shank portion has substantially the same diameter throughout,
    wherein said screw-handling end has substantially the same diameter as that of the elongate cylindrical body and comprises a plurality of flats extending parallel to an axis defined by said cylinder body at a predetermined spacing over a main portion of the smooth shank portion unoccupied by the thread and alternating with separation lands.

2. The bone screw according to claim 1, wherein another plurality of flats corresponds, at an angularly shifted location on said cylinder body, to said plurality of flats.

3. The bone screw according to claim 2, wherein a flat corresponds to a separation land of said another plurality of flats formed at angularly shifted locations.

4. The bone screw according to claim 2, wherein said flats are joined to said lands by a radiused step.

5. The bone screw according to claim 1, wherein another plurality of flats corresponds, at a diametrically opposite location on said cylinder body, to said plurality of flats.

6. The bone screw according to claim 5, wherein a flat corresponds to a separation land of said another plurality of flats formed at diametrically opposite locations.

7. The bone screw according to claim 1, wherein said flats are rectangular in shape and have the same dimensions.

* * * * *